(12) United States Patent
Heckroth et al.

(10) Patent No.: US 10,633,481 B2
(45) Date of Patent: *Apr. 28, 2020

(54) POLYUREA SYSTEMS, PROCESSES FOR PREPARING THE SAME AND USE THEREOF FOR POSTOPERATIVE ADHESION BARRIERS

(71) Applicant: Adhesys Medical GmbH, Aachen (DE)

(72) Inventors: Heike Heckroth, Odenthal (DE); Hartmut Nefzger, Pulheim (DE); Christian Wamprecht, Neuss (DE)

(73) Assignee: Adhesys Medical GmbH (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/635,472

(22) Filed: Mar. 2, 2015

(65) Prior Publication Data

US 2015/0166715 A1   Jun. 18, 2015

Related U.S. Application Data

(63) Continuation of application No. 12/370,639, filed on Feb. 13, 2009, now Pat. No. 9,000,089.

(30) Foreign Application Priority Data

Feb. 28, 2008 (EP) ..................... 08003620

(51) Int. Cl.
| | |
|---|---|
| C08G 18/38 | (2006.01) |
| A61L 31/06 | (2006.01) |
| C08G 18/10 | (2006.01) |
| C08G 18/42 | (2006.01) |
| C08G 18/48 | (2006.01) |
| C08G 18/73 | (2006.01) |
| C08G 18/76 | (2006.01) |
| C08G 18/32 | (2006.01) |
| A61L 15/26 | (2006.01) |
| A61L 31/14 | (2006.01) |

(52) U.S. Cl.
CPC .......... *C08G 18/3821* (2013.01); *A61L 15/26* (2013.01); *A61L 31/06* (2013.01); *A61L 31/148* (2013.01); *C08G 18/10* (2013.01); *C08G 18/3262* (2013.01); *C08G 18/4252* (2013.01); *C08G 18/485* (2013.01); *C08G 18/4841* (2013.01); *C08G 18/73* (2013.01); *C08G 18/7621* (2013.01); *A61L 2430/00* (2013.01); *Y10T 428/31551* (2015.04); *Y10T 428/31594* (2015.04)

(58) Field of Classification Search
CPC .... C08G 18/3821; C08G 18/73; C08G 18/10; C08G 18/4252; C08G 18/3262
See application file for complete search history.

(56) References Cited

U.S. PATENT DOCUMENTS

| | | | | |
|---|---|---|---|---|
| 4,092,275 | A | * | 5/1978 | Reischl ................. C08G 18/08 521/137 |
| 4,141,973 | A | | 2/1979 | Balazs |
| 4,324,716 | A | * | 4/1982 | Reischl .............. C08G 18/0804 521/117 |
| 4,532,134 | A | | 7/1985 | Malette et al. |
| 4,701,480 | A | | 10/1987 | Markusch et al. |
| 4,886,787 | A | | 12/1989 | de Belder et al. |

(Continued)

FOREIGN PATENT DOCUMENTS

| | | |
|---|---|---|
| DE | 69929278 T2 | 10/1999 |
| DE | 10246708 A1 | 4/2004 |

(Continued)

OTHER PUBLICATIONS

S.G. Temel, et al., "A New Material for Prevention of Epidural Fibrosis After Laminectomy," *J Spinal Disord Tech*, Jun. 2006, pp. 270-275, vol. 19, No. 4.

(Continued)

*Primary Examiner* — Michael L Leonard
(74) *Attorney, Agent, or Firm* — Faegre Drinker Biddle & Reath LLP

(57) ABSTRACT

Polyurea systems comprising: (a) an amino-functional aspartic ester of the general formula (I)

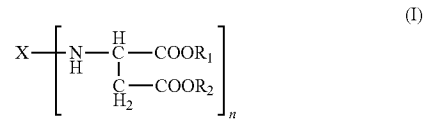

wherein X represents an n-valent organic radical derived from a corresponding n-functional primary amine $X(NH_2)_n$, $R_1$ and $R_2$ each independently represent an organic radical having no Zerevitinov active hydrogens and n represents an integer of at least 2; and (b) an isocyanate functional prepolymer having a residual monomer content of less than 1% by weight, the prepolymer prepared by reacting: (b1) an aliphatic isocyante; and (b2) a polyol component having a number average molecular weight of ≥400 g/mol and an average OH functionality of 2 to 6, wherein the polyol component comprises one or more constituents selected from the group consisting of polyester polyols, polyesterpolyether polyols and mixtures thereof; processes for making the same; postoperative adhesions barriers prepared therewith and dispensing systems for such polyurea systems.

14 Claims, No Drawings

(56) References Cited

U.S. PATENT DOCUMENTS

| | | | |
|---|---|---|---|
| 4,911,926 A | 3/1990 | Henry et al. | |
| 4,994,277 A | 2/1991 | Higham et al. | |
| 5,093,319 A | 3/1992 | Higham et al. | |
| 5,126,170 A * | 6/1992 | Zwiener | C08G 18/3821 427/385.5 |
| 5,135,751 A | 8/1992 | Henry et al. | |
| 5,243,012 A | 9/1993 | Wicks et al. | |
| 5,246,698 A | 9/1993 | Leshchiner et al. | |
| 5,266,326 A | 11/1993 | Barry et al. | |
| 5,356,883 A | 10/1994 | Kuo et al. | |
| 5,366,735 A | 11/1994 | Henry | |
| 5,462,976 A | 10/1995 | Matsuda et al. | |
| 5,466,771 A | 11/1995 | Hicks et al. | |
| 5,583,114 A | 12/1996 | Barrows et al. | |
| 5,605,938 A | 2/1997 | Roufa et al. | |
| 5,605,939 A * | 2/1997 | Hager | C08G 18/4072 521/137 |
| 5,612,052 A | 3/1997 | Shalaby | |
| 5,679,658 A | 10/1997 | Elson | |
| 5,681,576 A | 10/1997 | Henry | |
| 5,714,159 A | 2/1998 | Shalaby | |
| 6,013,755 A | 1/2000 | Primeaux, II et al. | |
| 6,063,863 A | 5/2000 | Yu et al. | |
| 6,136,333 A | 10/2000 | Cohn et al. | |
| 6,174,984 B1 * | 1/2001 | Peter | C08G 18/10 301/5.301 |
| 6,413,539 B1 | 7/2002 | Shalaby | |
| 6,514,534 B1 | 2/2003 | Sawhney | |
| 6,551,610 B2 | 4/2003 | Shalaby et al. | |
| 6,586,483 B2 | 7/2003 | Kolb et al. | |
| 6,762,241 B1 | 7/2004 | Blum et al. | |
| 7,001,948 B2 | 2/2006 | Gupta et al. | |
| 7,025,990 B2 | 4/2006 | Sawhney | |
| 7,129,300 B2 | 10/2006 | Roby | |
| 7,754,782 B2 * | 7/2010 | Heckroth | A61L 24/046 424/423 |
| 8,703,167 B2 | 4/2014 | Glauser et al. | |
| 8,772,407 B2 | 7/2014 | Mowrer | |
| 2003/0077242 A1 | 4/2003 | Sawhney | |
| 2004/0067315 A1 | 4/2004 | Niesten et al. | |
| 2004/0068078 A1 | 4/2004 | Milbocker | |
| 2004/0167255 A1 | 8/2004 | Lee et al. | |
| 2005/0175659 A1 | 8/2005 | Macomber et al. | |
| 2005/0266086 A1 | 12/2005 | Sawhney | |
| 2005/0271727 A1 | 12/2005 | Yao | |
| 2007/0100112 A1 * | 5/2007 | Sarpeshkar | C08G 18/10 528/44 |
| 2007/0129505 A1 | 6/2007 | Hadba et al. | |
| 2008/0306176 A1 * | 12/2008 | Nefzger | C08G 18/10 521/157 |
| 2009/0012206 A1 * | 1/2009 | Heckroth | A61L 24/046 523/111 |
| 2009/0191145 A1 * | 7/2009 | Heckroth | A61L 24/046 424/78.06 |

FOREIGN PATENT DOCUMENTS

| | | | |
|---|---|---|---|
| EP | 1081171 A2 * | 3/2001 | C08G 18/10 |
| EP | 1081171 A2 | 3/2001 | |
| EP | 1719530 A2 | 11/2006 | |
| EP | 2011808 A1 | 1/2009 | |
| EP | 2083025 A1 | 7/2009 | |
| WO | WO-00/09087 A1 | 2/2000 | |
| WO | WO-2004/021983 A2 | 3/2004 | |
| WO | WO-2006/010278 A1 | 2/2006 | |
| WO | WO-2007/067624 A2 | 6/2007 | |

OTHER PUBLICATIONS

Winship, Toxicity of Tin and its Compounds Adverse Drug Reac Acute Poisoning Rev. 1988, Spring, vol. 7, No. 1, pp. 19-38, Abstract From Pub Med—{http://www.ncbi.nim.nih.gov/pubmed/3291572}.

Acros MSDS Dibutyltin Diacetate. production No. 75959 Creation Date Jun. 1999.

C. Uglea Oligomer Technology and Applications, Marcel Dekker New York 1998, pp. 252-253.

European Office Action for European Application No. 16 170 678.3-1110, dated Apr. 11, 2018.

* cited by examiner

POLYUREA SYSTEMS, PROCESSES FOR PREPARING THE SAME AND USE THEREOF FOR POSTOPERATIVE ADHESION BARRIERS

RELATED APPLICATIONS

This application is a continuation of U.S. patent application Ser. No. 12/370,639, filed Feb. 13, 2009, which claims priority to European Application No. 08003620.5, filed Feb. 28, 2008. Each disclosure of the aforementioned priority applications is incorporated herein by reference in its entirety.

BACKGROUND OF THE INVENTION

Adhesions are among the most frequent complications after interventions in the abdominal and pelvic region. Adhesions are fibrous bands which generally form within the first seven days after an operation, in the course of the healing process. They cause tissues and organs which are normally separated from one another to grow together, which can give rise to a multiplicity of complications such as, for example, chronic pain, infertility or a life-treating intestinal occlusion. Products able to reduce the formation of adhesions have been developed in recent years to avoid such complications. Success has so far been limited, however.

Methods of preventing adhesions are peritoneal cavity lavage; the use of pharmacologically active agents such as anti-inflammatories or fibrinolytics; and also the application of mechanical barriers to separate the tissue. Adhesion barriers consist of an inert or absorbable material which is applied to the organs in question. Research has been done on a multiplicity of materials such as polysaccharides (U.S. Pat. No. 4,886,787, U.S. Pat. No. 5,356,883), hyaluronic acid U.S. Pat. No. 4,141,973, U.S. Pat. No. 5,246,698), alginates (U.S. Pat. No. 5,266,326), chitin (U.S. Pat. No. 5,093,319), chitosan (U.S. Pat. No. 4,532,134, U.S. Pat. No. 5,679,658), xanthan (U.S. Pat. No. 4,994,277), dextran (U.S. Pat. No. 5,605,938), cellulose and derivatives thereof (Journal of spinal disorders & techniques (2006), 19(4), 270-5), human serum albumin (U.S. Pat. No. 5,583,114), collagen (US 2005175659), glucosamine (U.S. Pat. No. 5,462,976), polyoxyalkylene copolymers (U.S. Pat. No. 4,911,926, U.S. Pat. No. 5,366,735, U.S. Pat. No. 5,135,751, U.S. Pat. No. 5,681,576), polyester (U.S. Pat. No. 5,612,052, U.S. Pat. No. 6,136,333), etc. A large proportion of these materials have not been commercialized for lack of efficacy, lack of bio-absorbability or because of interactions with the wound-healing process.

Commercially available products in membrane form such as INTERCEED™ (Johnson & Johnson), SEPRAFILM™ (Genzyme Corp.) and REPEL-CV™ (Life Medical Corp.), are absorbed within 28 days. However, since the barriers are laid onto the organ in question, there is a risk of slippage.

Barriers which like the hyaluronic acid derivative SEPRACOAT™ (GenzymeCorp.) and LUBRICOAT™ (Lifecore Biomedical Inc.) are applied as a liquid are often too quickly degraded by the body, limiting their barrier effect. In addition, there is a risk of migration and hence of no protective effect at all.

Hydrogels are water-containing polymers whose chains are linked covalently to form a three-dimensional network. In water, they swell rapidly and with a substantial increase in volume. Owing to their high water content, they are being investigated for use as adhesion barriers. As well as the hydrogels based on natural polysaccharides (alginates, hyaluronic acid) it is in particular hydrophilic polyethylene glycol-based systems (US 2005266086, DE-A 69929278, U.S. Pat. No. 7,025,990, U.S. Pat. No. 6,514,534, US 2003/0077242), such as the commercially available SPRAY-GEL™ (Confluent Surgical), which have been the subject of intensive research. Disadvantages found include the occasionally excessive rate of degradation and the acidity of the degradation products of lactic acid-based polyesters. As well as the polyethylene glycol-based hydrogel formation, there are frequent mentions (WO 0009087, US 20030077242, US 20050271727) of the redox-initiated free-radical polymerization. Redox initiators used include ascorbic acid and peroxides. As well as possible tissue irritation, one of the problems which arises is the aqueous consistency of the two reactants which is responsible for the absence of bonding to the organ in question.

Isocyanate-capped polymers such as polyester- and polyether-urethanes are described in US 2004/0068078 and WO 2004/021983 for uses including as postoperative adhesion barriers. Isocyanates used are preferably TDI (toluylene diisocyanate) and IPDI (isophorone diisocyanate), the prepolymers containing 0.05 to 1 mEq of low molecular weight polyisocyanaes such as monomeric TDI to promote adherence to the tissue being treated. In the presence of significant biological fluid, or in adherence to certain types of tissue, greater amounts thereof should preferably be present. Adherence develops inter alia through reaction of the isocyanate with the tissue. However, monomeric isocyanates, as well as tissue irritation, are known to lead to a sensitization and hence to allergic reactions. The reaction rate of the prepolymer on the tissue is substantially slowed when aliphatic isocyanates such as HDI are used, and therefore such a system is not practicable for clinical use.

U.S. Pat. No. 7,129,300 describes the production of absorbable 2-component systems consisting of a polyethylene oxide having two or more amine substituents and a biodegradable diisocyanate or an isocyanate-capped polyethylene oxide with an absorbable diamine.

WO 2006/010278 describes the production and use of polyurethane prepolymers and polyurethane acrylates based on aliphatic isocyanates such as HDI. Chain extenders (curatives) used are low molecular weight diols, diamines, triols, triamines or oligomers and also physiologically active compounds. Organic zinc, tin, magnesium and iron compounds are used as a catalyst. The invention is useable inter alia as an adhesion barrier but also for various implants. However, the use of a catalyst generally leads to a substantial acceleration in the rate of curing of the polymer and hence to an increased evolution of heat. Usefulness for internal organs is limited as a result.

EP-A 1719530 describes the use of isocyanate-capped polyester macromers based on aliphatic dicarboxylic acids and dihydroxy components such as polyalkylene oxides or polyethylene glycols. Aromatic, aliphatic and alicyclic isocyanates are described as possible isocyanates. Prepolymers formed from aromatics-based isocyanates such as TDI (as recited in the examples) have a reported crosslinking time on tissue of 1-10 min. However, the use of aromatics-based isocyanates in the body where, like the adhesion barriers, the product is fully degraded must be considered problematical because of the cleavage products which form. Systems based on aliphatic isocyanates are known from experience to have insufficient reactivity and hence too slow a cure time for practicable use in vivo. In addition, the viscosities of the compounds recited in EP-A 1719530 are too high at an average of 60 000 mPas for application, and therefore a solvent has to be used.

WO 2007/067624 describes a bioabsorbable 2-component system consisting of an isocyanate prepolymer based on glycolide, lactide, ε-caprolactone, p-dioxanone, trimethyl carbonate and polyalkylene oxide (for example polyethylene glycols). The second component used is a polyamine. On application of the two components to tissue a gel is formed that is useful as an adhesive or as an adhesion barrier. However, the prepolymers have an extremely high viscosity and therefore are difficult to apply without added solvent. Possible solvents mentioned include water, alcohols and ketones. Hydroxyl-containing solvents, however, present the problem of rapid reaction with the prepolymer, so that there is a risk of gelling. Processing time, moreover, can become extremely rapid and thereby make processing problematical. The use of solvents in vivo must generally in most cases be considered problematical on account of possible cytotoxicity and also interaction with the tissue.

That aspartic esters are suitable in principle for crosslinking prepolymers is known in the prior art in the context of surface coatings and described in DE-A 10246708 or EP-A 1081171.

European patent application No. 07021764.1, unpublished at the priority date of the present invention, already describes wound adhesives based on a combination of hydrophilic polyisocyanate prepolymers and aspartates as hardeners. The prepolymers are based on polyether polyols and therefore are not biodegradable within 6 to 12 months. In addition, the systems described are strong adhesives and therefore unsuitable for use as an adhesion barrier.

BRIEF SUMMARY OF THE INVENTION

The present invention relates to novel adhesion barriers based on hydrophilic polyisocyanate prepolymers for use in surgery.

Various embodiments of the present invention can provide adhesion barriers which: form a flexible film on the organs/tissue to be protected; adhere to the organs/tissue to be protected; are biodegradable in a time window of up to 6 months; are biocompatible; form degradation products without cell and tissue toxicity; solidify rapidly in keeping with the use; display no significant, tissue-damaging exotherm in curing; are easy to apply and unable to penetrate into deeper layers of tissue.

Tissue in the context of the present invention is to be understood as meaning cell assemblages consisting of cells of the same shape and function such as epithelial tissue, myocardial tissue, connective or stroma tissue, muscles, nerves and cartilage. Also included are all organs constructed of cell assemblages such as the liver, kidneys, lungs, heart, uterus, etc.

It has now been found that such advantageous adhesion barriers can be achieved by a combination of isocyanate-functional polyester prepolymers based on aliphatic isocyanates having residual monomer contents of less than 1% by weight in combination with amino-functional aspartic esters. Crosslinking catalysts are not needed for crosslinking on the tissue.

The present invention accordingly provides polyurea systems comprising

A) amino-functional aspartic esters of the general formula (I)

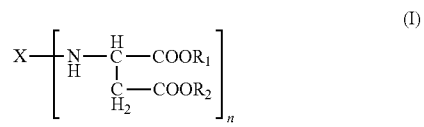

where X is an n-valent organic radical obtained by removal of the primary amino groups of an n-functional amine, $R_1$, $R_2$ are the same or different organic radicals devoid of any Zerevitinov-active hydrogen and n is an integer of at least 2 and B) isocyanate-functional prepolymers having residual monomer contents of less than 1% by weight, preferably less than 0.1% by weight and more preferably less than 0.03% by weight, obtainable by reaction of B1) aliphatic isocyanates with B2) a polyol component having number average molecular weights of ≥400 g/mol and average OH functionalities of 2 to 6 which contains polyester polyols and/or polyester-polyether polyols and also optionally polyether polyols and C) optionally, organic fillers having a DIN 53019 viscosity at 23° C. in the range from 10 to 6000 mPas, and D) where appropriate, reaction products of isocyanate-functional prepolymers as per the definition of component B) with aspartic esters as per component A) and/or organic fillers as per C).

One embodiment of the present invention includes a polyurea system comprising:

(a) an amino-functional aspartic ester of the general formula (I)

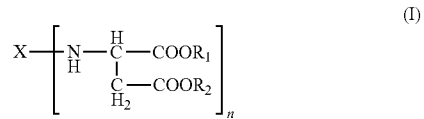

wherein X represents an n-valent organic radical derived from a corresponding n-functional primary amine $X(NH_2)_n$, $R_1$ and $R_2$ each independently represent an organic radical having no Zerevitinov active hydrogens and n represents an integer of at least 2; and (b) an isocyanate functional prepolymer having a residual monomer content of less than 1% by weight, the prepolymer prepared by reacting:

(b1) an aliphatic isocyante; and (b2) a polyol component having a number average molecular weight of ≥400 g/mol and an average OH functionality of 2 to 6, wherein the polyol component comprises one or more constituents selected from the group consisting of polyester polyols, polyester-polyether polyols and mixtures thereof.

Another embodiment of the present invention includes a process for preparing a polyurea system, the process comprising:

(i) providing (a) an amino-functional aspartic ester of the general formula (I)

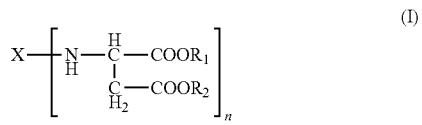

wherein X represents an n-valent organic radical derived from a corresponding n-functional primary amine $X(NH_2)_n$, $R_1$ and $R_2$ each independently represent an organic radical having no Zerevitinov active hydrogens and n represents an integer of at least 2;

(ii) providing (b) an isocyanate functional prepolymer having a residual monomer content of less than 1% by weight, the prepolymer prepared by reacting:

(b1) an aliphatic isocyante; and (b2) a polyol component having a number average molecular weight of ≥400 g/mol and an average OH functionality of 2 to 6, wherein the polyol component comprises one or more constituents selected from the group consisting of polyester polyols, polyester-polyether polyols and mixtures thereof; and (iv) mixing the (a) amino-functional aspartic ester and the (b) isocyanate functional prepolymer in a ratio of free or blocked amino groups to free NCO groups of 1:1.

Another embodiment of the present invention includes a dispensing system comprising a first chamber and a second chamber; wherein the first chamber comprises (a) an amino-functional aspartic ester of the general formula (I)

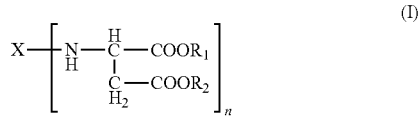

wherein X represents an n-valent organic radical derived from a corresponding n-functional primary amine $X(NH_2)_n$, $R_1$ and $R_2$ each independently represent an organic radical having no Zerevitinov active hydrogens and n represents an integer of at least 2; and wherein the second chamber comprises (b) an isocyanate functional prepolymer having a residual monomer content of less than 1% by weight, the prepolymer prepared by reacting:

(b1) an aliphatic isocyante; and (b2) a polyol component having a number average molecular weight of ≥400 g/mol and an average OH functionality of 2 to 6, wherein the polyol component comprises one or more constituents selected from the group consisting of polyester polyols, polyester-polyether polyols and mixtures thereof.

Yet another embodiment of the present invention includes a method comprising: (i) providing cell tissue to be treated; (ii) providing a polyurea system according any of the various embodiments of the invention; and (iii) contacting the cell tissue to be treated with the polyurea system.

Still other embodiments of the present invention include postoperative adhesion barriers and films comprising polyurea systems according any of the various embodiments of the invention.

For the definition of Zerevitinov-active hydrogen, reference is made to Rompp Chemie Lexikon, Georg Thieme Verlag Stuttgart. Groups having Zerevitinov-active hydrogen are preferably understood as meaning OH, NH or SH.

DETAILED DESCRIPTION OF THE INVENTION

As used herein, the singular terms "a" and "the" are synonymous and used interchangeably with "one or more" and "at least one," unless the language and/or context clearly indicates otherwise. Accordingly, for example, reference to "an aliphatic isocyanate" herein or in the appended claims can refer to a single aliphatic isocyanate or more than one aliphatic isocyanate. Additionally, all numerical values, unless otherwise specifically noted, are understood to be modified by the word "about."

Preferred meanings in the formula (I) are:

$R_1$, $R_2$ are the same or different optionally branched or cyclic organic radicals devoid of any Zerevitinov-active hydrogen and having 1 to 20 and preferably 1 to 10 carbon atoms, more preferably methyl or ethyl, n is an integer from 2 to 4, and X is an n-valent organic optionally branched or cyclic organic radical having 2 to 20, preferably 5 to 10 carbon atoms, obtained by removing the primary amino groups of an n-functional primary amine.

It will be appreciated that mixtures of two or more aspartic esters can also be used, and therefore n in the formula (I) may also be a non-integral mean value.

The amino-functional polyaspartic esters A) can be prepared in a known manner by reaction of the corresponding primary at least difunctional amines $X(NH_2)_n$ with maleic or fumaric esters of the general formula

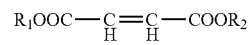

Preferred maleic or fumaric esters include dimethyl maleinate, diethyl maleinate, dibutyl maleinate and the corresponding fumaric esters.

Preferred primary at least difunctional amines $X(NH_2)_n$ include ethylenediamine, 1,2-diaminopropane, 1,4-diaminobutane, 1,3-diaminopentane, 1,5-diaminopentane, 2-methyl-1,5-diaminopentane, 1,6-diaminohexane, 2,5-diamino-2,5-dimethylhexane, 2,2,4- and/or 2,4,4-trimethyl-1,6-diaminohexane, 1,11-diaminoundecane, 1,12-diaminododecane, 1-amino-3,3,5-trimethyl-5-aminomethylcyclohexane, 2,4- and/or 2,6-hexahydrotoluylenediamine, 2,4'- and/or 4,4'-diaminodicyclohexylmethane, 3,3'-dimethyl-4,4'-diaminodicyclohexylmethane, 2,4,4'-triamino-5-methyldicyclohexylmethane and polyetheramines having aliphatically attached primary amino groups having a number average molecular weight $M_n$ in the range from 148 to 6000 g/mol.

Particularly preferred primary at least difunctional amines are 1,3-diaminopentane, 1,5-diaminopentane, 2-methyl-1,5-diaminopentane, 1,6-diaminohexane, 1,13-diamino-4,7,10-trioxatridecane. 2-Methyl-1,5-diaminopentane is very particularly preferred.

In some preferred embodiments of the invention, $R_1=R_2=$ethyl and X is based on 2-methyl-1,5-diaminopentane as n-functional amine.

The preparation of the amino-functional aspartic esters A) from the starting materials mentioned can be effected according to U.S. Pat. No. 5,243,012, the entire contents of which are hereby incorporated herein by reference, preferably within the temperature range from 0 to 100° C., the starting materials being used in such ratios that for each primary amino group there is at least one, preferably exactly one, olefinic double bond, any starting materials used in excess being removable by distillation after the reaction. The reaction can be carried out without a solvent or in the presence of suitable solvents such as methanol, ethanol, propanol, dioxane or mixtures thereof.

The systems according to the present invention can be obtained by mixing the prepolymers B) with the amino-functional aspartic esters A) and also where appropriate the components C) and/or D). The ratio of free or blocked amino groups to free NCO groups is preferably 1:1.5 and more preferably 1:1.

Immediately after the individual components have been mixed together, the systems according to the present invention have a DIN 53019 shear viscosity at 23° C. of preferably 500 to 20 000 mPas and more preferably 500 to 8000 mPas.

The time for complete crosslinking and curing of the adhesion barrier typically is in the range from 30 s to 10 min at 23° C., preferably in the range from 30 s to 8 min and more preferably in the range from 1 min to 5 min.

The isocyanate-functional prepolymers used in B) can be obtained by reaction of isocyanates B1) with polyols B2) in the presence or absence of catalysts and also auxiliary and additive materials.

The isocyanates or isocyanate mixtures used in B1) preferably have an average NCO functionality in the range from 2 to 2.6 and more preferably in the range from 2 to 2.4. B1) may utilize as isocyanates, for example, monomeric aliphatic or cycloaliphatic di- or triisocyanates such as 1,4-butylene diisocyanate (BDI), 1,6-hexamethylene diisocyanate (HDI), isophorone diisocyanate (IPDI), 2,2,4- and/or 2,4,4-trimethylhexamethylene diisocyanate, the isomeric bis (4,4'-isocyanatocyclohexyl)methanes or their mixtures of any desired isomeric content, 1,4-cyclohexylene diisocyanate, 4-isocyanatomethyloctane 1,8-diisocyanate (nonane triisocyanate) and also alkyl 2,6-diisocyanatohexanoate (lysine diisocyanate) having C1-C8-alkyl groups.

As well as the aforementioned monomeric isocyanates, it is also possible to use their higher molecular weight descendent products of uretdione, isocyanurate, urethane, allophanate, biuret, iminooxadiazinedione or oxadiazinetrione structure and also mixtures thereof. B1) preferably utilizes isocyanates of the aforementioned kind with exclusively aliphatically or cycloaliphatically attached isocyanate groups or mixtures thereof. Hexamethylene diisocyanate is very particularly preferred for use in B1).

Polyol component B2) preferably utilizes polyols having an average OH functionality in the range from 2.3 to 4. B2) preferably utilizes polyether ester polyols and preferably their mixtures with polyether polyols.

Such preferred polyether ester polyols having a hydroxyl number of 30 to 140 mg KOH/g, preferably 35 to 130 mg KOH/g, and also an acid number of 0.05 to 10 mg KOH/g, preferably 0.1 to 3 mg KOH/g and more preferably 0.15 to 2.5 mg KOH/g.

Polyether esters essential to the present invention are liquid at room temperature and have a DIN 53019 shear viscosity at 23° C. of 200 to 8000 mPas, preferably 400 to 4000 mPas.

Such polyether ester polyols are preferably prepared by polycondensation of polycarboxylic acids, anhydrides of polycarboxylic acids and also esters of polycarboxylic acids with volatile alcohols, preferably C1 to C6 monools, such as methanol, ethanol, propanol or butanol, with (in molar terms) excess, low molecular weight and/or higher molecular weight polyol; the polyol used comprises polyols containing ether groups with or without other polyols free of ether groups.

It will be appreciated that polyether ester synthesis may also utilize mixtures of the higher molecular weight polyols and of the low molecular weight polyols.

Such (in molar terms) excess low molecular weight polyols are polyols having molar masses of 62 to 299 daltons, having 2 to 12 carbon atoms and hydroxyl functionalities of at least 2, which may further be branched or unbranched and whose hydroxyl groups are primary or secondary. These low molecular weight polyols can also have ether groups. Typical representatives are ethylene glycol, 1,2-propanediol, 1,3-propanediol, 1,4-butanediol, 2,3-butanediol, 2-methyl-1,3-propanediol, 1,5-pentanediol, 1,6-hexanediol, 3-methyl-1,5-pentanediol, 1,8-octanediol, 1,10-decanediol, 1,12-dodecanediol, cyclohexanediol, diethylene glycol, triethylene glycol and higher homologues, dipropylene glycol, tripropylene glycol and higher homologues, glycerol, 1,1,1-trimethylolpropane and also oligotetrahydrofurans having hydroxyl end groups. It will be appreciated that mixtures can also be used within this group.

Higher molecular weight polyols excess in molar terms are polyols having molar masses of 300 to 3000 daltons, which are obtained by ring-opening polymerization of epoxides, preferably ethylene oxide and/or propylene oxide, and also by acid-catalysed, ring-opening polymerization of tetrahydrofuran. Ring-opening polymerization of epoxides may utilize either alkali metal hydroxides or double metal cyanide catalysts.

Useful starters for ring-opening polymerization of epoxides include all at least bifunctional molecules from the group of the amines and the abovementioned low molecular weight polyols. Typical representatives are 1,1,1-trimethylolpropane, glycerol, o-TDA, ethylenediamine, 1,2-propylene glycol, etc. and also water, including mixtures thereof. It will be appreciated that mixtures can also be used within the group of excess higher molecular weight polyols.

The construction of the higher molecular weight polyols comprising hydroxyl-terminated polyalkylene oxides formed from ethylene oxide and/or propylene oxide may be effected randomly or blockwise, in which case mixed blocks can be present as well.

Polycarboxylic acids are aliphatic and aromatic carboxylic acids which can be cyclic, linear, branched or unbranched and which have between 4 and 24 carbon atoms.

Examples are succinic acid, glutaric acid, adipic acid, azelaic acid, sebacic acid, 1,10-decanedicarboxylic acid, 1,12-dodecanedicarboxylic acid, phthalic acid, terephthalic acid, isophthalic acid, trimellitic acid, pyromellitic acid. Preference is given to succinic acid, glutaric acid, adipic acid, sebacic acid, lactic acid, phthalic acid, terephthalic acid, isophthalic acid, trimellitic acid, pyromellitic acid. Particular preference is given to succinic acid, glutaric acid and adipic acid.

The group of the polycarboxylic acids further comprises hydroxy carboxylic acids or inner anhydrides thereof, for example caprolactone, lactic acid, hydroxybutyric acid, ricinolic acid, etc. Also included are monocarboxylic acids, in particular those having more than 10 carbon atoms, such as soybean oil fatty acid, palm oil fatty acid and groundnut oil fatty acid, subject to the proviso that their proportion of the total reaction mixture constructing the polyether ester polyol does not exceed 10% by weight and additionally the resulting lesser functionality is compensated by co-use of at least trifunctional polyols, whether as part of the low molecular weight polyols or as part of the high molecular weight polyols.

The preparation of the polyether ester polyol can be effected in accordance with known methods at elevated temperature in the range from 120 to 250° C., initially under atmospheric pressure, later by applying a vacuum of 1 to 100 mbar, preferably but not necessarily with use of an esterification or transesterification catalyst, the reaction being completed to such an extent that the acid number decreases to values in the range from 0.05 to 10 mg KOH/g, preferably 0.1 to 3 mg KOH/g and more preferably 0.15 to 2.5 mg KOH/g.

Furthermore, an inert gas can be used as part of the atmospheric pressure phase before a vacuum is applied. It will be appreciated that liquid or gaseous entrainers can also be used alternatively or for individual phases of the esterification. For example, the water of reaction can be removed using nitrogen as a carrier gas, but also with the use of an azeotropic entrainer, for example benzene, toluene, xylene, dioxane, etc.

The polyether polyols optionally used in B2 as a blending component have a molecular weight in the range from 100 to 2000 g/mol, preferably in the range from 100 to 1000 g/mol and more preferably in the range from 100 to 400 g/mol and consist wholly or partly of polyethylene oxide polyols.

When B2 utilizes polyether polyols alongside the polyesters or polyether esters, their proportion will comprise not more than 70% by weight and preferably not more than 50% by weight based on the entire component B2.

Preferably the mass fraction of the entire component B2 that is attributable to ethylene oxide is preferably in the range from 40% to 95% by weight and more preferably in the range from 60% to 90% by weight.

Component B2 preferably has an ester group concentration (in moles per kg) of 0.5 to 5.5 and more preferably 1 to 3.5.

The prepolymers prepared from B1 and B2 have a DIN EN ISO 11909 average NCO content of 2% to 10% by weight and preferably 2.5% to 8% by weight.

The organic liquid fillers used in C) are preferably non-cytotoxic as per ISO 10993 cytotoxicity measurement.

Useful organic fillers include for example 23° C. liquid polyethylene glycols such as PEG 200 to PEG 600, their monoalkyl and dialkyl ethers such as PEG 500 dimethyl ether, liquid polyether and polyester polyols, liquid polyesters such as, for example, Ultramoll (Lanxess AG, Leverkusen, Germany), and also glycerol and its liquid derivatives such as, for example, Triacetin (Lanxess AG, Leverkusen, Germany).

The organic fillers of component C) preferably comprise hydroxy- or amino-functional, preferably purely hydroxy-functional compounds. Particular preference is given to polyols. Preferred polyols are polyethers and/or polyester polyols and more preferably polyether polyols. The preferred organic fillers preferably have average OH functionalities in the range from 1.5 to 3, more preferably in the range from 1.8 to 2.2 and more preferably 2.0. The preferred organic fillers of component preferably have repeat units derived from ethylene oxide. The viscosity of the organic fillers is preferably in the range from 50 to 4000 mPas, more preferably in the range from 50 to 2000 mPas at 23° C. measured to DIN 53019.

Certain preferred embodiments of the invention utilizes polyethylene glycols as organic fillers. These polyethylene glycols preferably have a number average molecular weight in the range from 100 to 1000 g/mol and more preferably in the range from 200 to 400 g/mol.

The weight ratio of the filler component C) to the aspartate component A) is generally in the range from 0:1 to 20:1 and preferably in the range from 0:1 to 12:1.

The weight ratio of the filler relative to the total amount of the mixture of A, and B is generally in the range from 0 to 100% and preferably in the range from 0 to 60%.

To further reduce the average equivalent weight of all the compounds used for prepolymer crosslinking, based on the NCO-reactive groups, it is also possible, in addition to the compounds used in A), to prepare the amino- or hydroxy-functional reaction products of isocyanate-functional copolymers with aspartic esters and/or organic fillers, provided the latter are amino- or hydroxy-functional, in a separate prereaction and then to use these reaction products as higher molecular weight curative component.

The pre-extending step preferably utilizes ratios of isocyanate-reactive groups to isocyanate groups in the range from 50:1 to 1.5:1 and more preferably in the range from 15:1 to 4:1.

The isocyanate-functional prepolymer to be used for this can correspond to that of component B) or else be constructed differently from the components listed as possible constituents of the isocyanate-functional prepolymers in the context of this application.

Modification through pre-extension has the advantage that the equivalent weight and equivalent volume of the curative component is modifiable within distinct limits. As a result, commercially available 2-chamber dispensing systems can be used for application in order to obtain an adhesive system which, given existing ratios for the chamber volumes, be fine tuned to the desired ratio of NCO-reactive groups to NCO groups.

The invention further provides a process for preparing the urea systems of the invention and also their use as an adhesive or coating for sealing, uniting or covering cell tissues. Covering cell tissues is preferably understood as meaning preparing postoperative adhesion barriers.

In the case of coatings for preparing postoperative adhesion barriers, it can be sensible to colour one or more of the components A) to D) used to make the barrier easier to see.

In the in vivo application of a coating to produce a postoperative adhesion barrier, the necessary components are applied, with the aid of a two-chamber dispensing system and a suitable applicator, to the organ to be protected and there form a protective polymeric film within 10 minutes. This polymeric film adheres to the organ surface without penetrating into the tissue. The film can be mechanically removed without damaging the tissue. The invention further provides the present urea systems for preparing means for sealing, uniting or covering cell tissues. Similarly, films and composite parts are obtainable using the urea systems of the present invention.

The invention will now be described in further detail with reference to the following non-limiting examples.

EXAMPLES

Unless stated otherwise, all percentages are by weight.

Example A

Aspartate Synthesis

To 2 mol of diethyl maleate was gradually added dropwise 1 mol of 2-methyl-1,5-diaminopentane under nitrogen atmosphere such that the reaction temperature does not exceed 60° C. The reaction mixture was then heated at 60° C. until diethyl maleate was no longer detectable in the reaction mixture.

Example B

Polyester Synthesis

Raw Materials

Polyether 1 is a 1,2-propylene glycol-started, KOH-catalysed polyether glycol from BMS AG having a hydroxyl number of 56 mg KOH/g and having about 50% by weight each of ethylene oxide and propylene oxide units, the chain ends being tipped with ethylene oxide.

Polyether 2 is a 1,2-propylene glycol-started, KOH-catalysed, hydroxyl-terminated polyethylene oxide from BMS AG having a hydroxyl number of 190 mg KOH/g.

Polyether 3 is a 1,1,1-trimethylolpropane-started, KOH-catalysed, hydroxyl-terminated polyethylene oxide from BMS AG having an hydroxyl number of 550 mg KOH/g.

The ester group concentration portrayed in Table 1 corresponds to the number of moles of carboxyl groups used for 1 kg of product.

The reported "fraction of ethylene oxide groups" computes from the ethylene oxide group content of the starting polyether 1 (50% by weight), polyether 2 (100%), polyether 3 (100%) and diethylene glycol (100%), or their proportion of the starting materials of the polyester recipe.

In a 6 l flask equipped with thermometer, column, reflux divider with head thermometer, descending condenser and 1 l receiver, 98 g (1.07 mol) of glycerol, 935 g (0.47 mol) of polyether 1, 1615 g (2.73 mol) of polyether 2 and 467 g (3.2 mol) of adipic acid were gradually heated to 200° C. at atmospheric pressure and under nitrogen with stirring, while water of reaction distilled off. After 5 hours, 68 mg of tin dichloride dihydrate were added and at the same time vacuum was applied to ultimately produce a pressure of 15 mbar. After a further 20 hours, the reaction had ended. Analysis gave the values recited in Table 1.

Example C

Prepolymer Synthesis

Example C-2a 236.95 g of HDI and 0.4 g of benzoyl chloride were placed as initial charge in a 500 ml four-neck flask. 162.6 g of polyester 2 from Example B-2, dewatered at 100° C., were added at 80° C. during 2 h and subsequently stirred in for 1 h. Then, thin film distillation at 140° C. and 0.1 Torr was used to distil off excess HDI (hexamethylene diisocyanate) to leave 280 g of the prepolymer having an NCO content of 5.67%. The residual monomer content was <0.03% of free HDI.

Example C-2b

Prepolymer-Synthesis 281.88 g of HDI and 0.4 g of benzoyl chloride were placed as initial charge in a 500 ml four-neck flask. A mixture of 96.75 g of polyester 2 from Example B-2 and 20.97 g of polyethylene glycol of molar mass 200 Da (PEG 200), dewatered at 100° C., were added at 80° C. during 2 h and subsequently stirred in for 1 h. Then, thin film distillation at 140° C. and 0.1 Torr was used to distil off excess HDI to leave 311 g of the prepolymer having an NCO content of 7.88%. The residual monomer content was <0.03% of free HDI.

Example C-2c

Prepolymer-Synthesis 267.82 g of HDI and 0.4 g of benzoyl chloride were placed as initial charge in a 500 ml four-neck flask. A mixture of 91.92 g of polyester 2 from Example B-2 and 39.85 g of PEG 400, dewatered at 100° C., were added at 80° C. during 2 h and subsequently stirred in for 1 h. Then, thin film distillation at 140° C. and 0.1 Torr was used to distil off excess HDI to leave 302 g of the prepolymer having an NCO content of 7.57%. The residual monomer content was <0.03% of free HDI.

TABLE 1

Synthesis and characterization of inventive polyester polyols, batch size per 3 kg of product

| Example | | B-1 | B-2 | B-3 | B-4 | B-5 | B-6 | B-7 | B-8 | B-9 | B-10 |
|---|---|---|---|---|---|---|---|---|---|---|---|
| adipic acid | [g] | 467 | 426 | 218 | 289 | 562 | | 733 | 493 | 201 | 292 |
| succinic acid | [g] | | | | | | 473 | | | | |
| glycerol | [g] | 98 | | 118 | 98 | | | | | 99 | 82 |
| TMP | [g] | | | | | | | | 256 | | |
| polyether 1 | [g] | 935 | 931 | 1527 | 2150 | | | 954 | 937 | 2748 | 2148 |
| polyether 2 | [g] | 1615 | 906 | 1191 | 534 | 1735 | 1829 | 326 | 1179 | | 546 |
| Polyether 3 | [g] | | 842 | | | 842 | 842 | 842 | 256 | | |
| diethylene glycol | [g] | | | | | | | 326 | | | |
| tin dichloride dihydrate | [mg] | 68 | 68 | 68 | 68 | 68 | 68 | 68 | 68 | 68 | 68 |
| functionality | | 3 | 3.5 | 2.5 | 3 | 3.5 | 3.5 | 3.5 | 3.5 | 3 | 3 |
| OH number exp. | [mg KOH/g] | 52.1 | 121.4 | 98.3 | 43.5 | 122 | 121 | 120 | 115 | 44.4 | 38.4 |
| acid number | [mg KOH/g] | 0.9 | 0.3 | 0.3 | 1.2 | 0.2 | 0.3 | 0.2 | 0.3 | 0.6 | 0.7 |
| viscosity | [mPas, 75° C.] | 620 | 180 | 100 | 440 | 2110 | 2490 | 3230 | 1850 | 2340 | 4450 |
| fraction of ethylene oxide units | [% by weight] | 67 | 71 | 64 | 52 | 82 | 85 | 69 | 61 | 45 | 53 |
| ester group concentration | [mol/kg] | 2.13 | 1.95 | 1.00 | 1.32 | 2.56 | 2.67 | 3.35 | 2.25 | 0.92 | 1.33 |

Example D

Production of Adhesion Barrier

Example D 10 g of prepolymer B were thoroughly mixed in a beaker with equivalent amounts of the amino-functional aspartic ester (aspartate A). The reaction mixture was immediately thereafter applied thinly to kidneys, liver and muscle tissue. Cure time and temperature and also adherence to the tissue were determined.

| Example prepolymer of polyester | D-1 C-1 | D-2a C-2a | D-2b C-2b | D-2c C-2c | D-3 C-3 | D-4 C-4 |
|---|---|---|---|---|---|---|
| NCO content of prepolymer [%] measured to DIN EN ISO 11909 | 3.06 | 5.67 | 7.88 | 7.57 | 4.38 | 2.57 |
| cure time [min] | 2 | 1 | 2 | 1.5 | 3 | 3 |
| cure temperature [° C.] | 35 | 40 | 41 | 40 | 42 | 35 |

| Example prepolymer of polyester | D-5 C-5 | D-6 C-6 | D-7 C-7 | D-8 C-8 | D-9 C-9 | D-10 C-10 |
|---|---|---|---|---|---|---|
| NCO content of prepolymer [%] | 5.95 | 5.92 | 6.0 | 5.72 | 2.01 | 2.07 |
| cure time [min] | 1.5 | 1 | 1 | 1.5 | 2 | 3 |
| cure temperature [° C.] | 41 | 43 | 42 | 47 | 28 | 37 |

A shiny, transparent film had formed at the reported times in all recited examples. Good adherence without penetration of the polymer into the tissue was observed in all cases. The barriers could be mechanically removed without damaging the tissue.

COMPARATIVE EXAMPLES

Example 1

When prepolymer A-1 was applied to tissue without aspartate admixture, no cure took place within 30 min.

Example 2

Prepolymer A-1 was prepared as described in Example B using TDI instead of HDI. The prepolymer obtained was admixed with different amounts of water and applied to tissue. No cure took place within 15 min.

Example 3

Synthesis of Polyether Polyol Prepolymer from EP 07021764.1

465 g of HDI and 2.35 g of benzoyl chloride were placed as initial charge in a 1 l four-neck flask. 931.8 g of a polyether having an ethylene oxide content of 63% and a propylene oxide content of 37% (each based on total alkylene oxide content) started on TMP (3-functional) were added at 80° C. during 2 h and subsequently stirred in for 1 h. Then, thin film distillation at 130° C. and 0.1 Torr was used to distil off excess HDI to leave 980 g (71%) of the prepolymer having an NCO content of 2.53%. The residual monomer content was <0.03% HDI.

Example 4

Adhesion Barrier 10 g of the prepolymer of Example 3 were thoroughly stirred in a beaker with equivalent amounts of the amino-functional aspartic ester (aspartate A). The reaction mixture was immediately thereafter applied thinly to kidneys, liver and muscle tissue. A cure took place within 2 min to form a transparent film. In the process, the polymer penetrated into the tissue and could not be removed without damage.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A polyurea system comprising:
    (a) an amino-functional aspartic ester of the general formula (I)

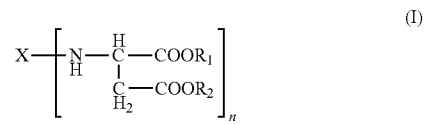

wherein
X is an n-valent organic radical having 2 to 5 carbon atoms,
$R_1$ and $R_2$ each independently represent an organic radical having no Zerevitinov active hydrogens and n represents an integer of at least 2;
    (b) an isocyanate functional prepolymer having a residual monomer content of less than 1% by weight, the prepolymer prepared by reacting:
        (b1) an aliphatic isocyante; and
        (b2) a polyol component comprising:
            a polyether polyol which has a number-average molecular weight of 100 to 2,000 g/mol; and
            a polyol component comprising one or more constituents selected from the group consisting of polyester polyols, polyester-polyether polyols and mixtures thereof having a number average molecular weight of ≥400 g/mol and an average OH functionality of 2 to 6;
            wherein the ether groups are derived from, 60% to 90% of ethylene oxide units, based on the amounts of alkylene oxide units that are present in total,
    (c) an organic filler comprising a hydroxy-functional polyether polyol compound having a DIN 53019 viscosity at 23° C. of 10 to 6000 mPas, and
wherein the ratio of free or blocked amino groups to free NCO groups is about 1:1.

2. The polyurea system according to claim 1, further comprising: (d) a reaction product of an isocyanate functional prepolymer according to (b) and an amino-functional aspartic ester according to (a).

3. The polyurea system according to claim 1, further comprising: (d) a reaction product of an isocyanate functional prepolymer according to (b); an amino-functional aspartic ester according to (a); and (c) an organic filler having a DIN 53019 viscosity at 23° C. of 10 to 6000 mPas.

4. The polyurea system according to claim 1, wherein the polyol component has a hydroxyl number of 30 to 140 mg KOH/g, an acid number of 0.05 to 10 mg KOH/g and a DIN 53019 shear viscosity at 23° C. of 200 to 8000 mPas.

5. The polyurea system according to claim 1, wherein the polyol component comprises ≤50% by weight of polyether polyols based on the polyol component.

6. The polyurea system according to claim 1, wherein the polyol component has an ester group concentrations of 0.5 to 5.5 moles per kg.

7. The polyurea system according to claim 1, further comprising: (d) a reaction product of an isocyanate functional prepolymer according to (b) and an amino-functional aspartic ester according to (a); wherein the polyol component has a hydroxyl number of 30 to 140 mg KOH/g, an acid number of 0.05 to 10 mg KOH/g and a DIN 53019 shear viscosity at 23° C. of 200 to 8000 mPas; wherein the polyol component comprises ≤50% by weight of polyether polyols based on the polyol component.

8. The polyurea system according to claim 1, wherein the weight ratio of the organic filler (c) to the amino-functional aspartic ester component (a) is from 0:1 to 12:1.

9. A process for preparing a polyurea system, the process comprising:
(i) providing (a) an amino-functional aspartic ester of the general formula (I)

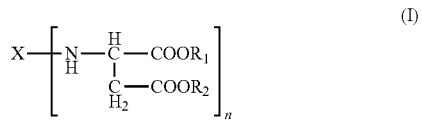

wherein
X is an n-valent organic radical having 2 to 5 carbon atoms, $R_1$ and $R_2$ each independently represent an organic radical having no Zerevitinov active hydrogens and n represents an integer of at least 2;
(ii) providing (b) an isocyanate functional prepolymer having a residual monomer content of less than 1% by weight, the prepolymer prepared by reacting:
(b1) an aliphatic isocyante; and
(b2) a polyol component comprising:
a polyether polyol which has a number-average molecular weight of 100 to 2,000 g/mol; and
a polyol component comprising one or more constituents selected from the group consisting of polyester polyols, polyester-polyether polyols and mixtures thereof having a number average molecular weight of ≥400 g/mol and an average OH functionality of 2 to 6;
wherein the ether groups are derived from, 60% to 90% of ethylene oxide units, based on the amounts of alkylene oxide units that are present in total;
(iii) providing (c) an organic filler comprising a hydroxy-functional polyether polyol compound having a DIN 53019 viscosity at 23° C. of 10 to 6000 mPas; and wherein the (c) organic filler is mixed with the (a) amino-functional aspartic ester and the (b) isocyanate functional prepolymer at a weight ratio of organic filler to amino-functional aspartic ester of 0:1 to 20:1; and
(iv) mixing the (a) amino-functional aspartic ester and the (b) isocyanate functional prepolymer in a ratio of free or blocked amino groups to free NCO groups of 1:1.

10. A polyurea system prepared according to the process of claim 9.

11. A method comprising:
(i) providing cell tissue to be treated;
(ii) providing a polyurea system according to claim 1; and
(iii) contacting the cell tissue to be treated with the polyurea system.

12. A post operative adhesion barrier comprising a polyurea system according to claim 1.

13. A film comprising a polyurea system according to claim 1.

14. A dispensing system comprising a first chamber and a second chamber; wherein the first chamber comprises (a) an amino-functional aspartic ester of the general formula (I)

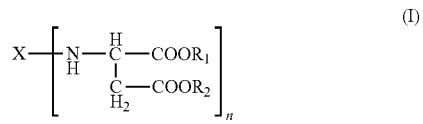

wherein
X is an n-valent organic optionally branched or cyclic organic radical having 2 to 5 carbon atoms,
$R_1$ and $R_2$ each independently represent an organic radical having no Zerevitinov active hydrogens and n represents an integer of at least 2; and wherein the second chamber comprises (b) an isocyanate functional prepolymer having a residual monomer content of less than 1% by weight, the prepolymer prepared by reacting:
(b1) an aliphatic isocyante; and
(b2) a polyol component comprising:
a polyether polyol which has a number-average molecular weight of 100 to 2,000 g/mol; and
a polyol component comprising one or more constituents selected from the group consisting of polyester polyols, polyester-polyether polyols and mixtures thereof having a number average molecular weight of ≥400 g/mol and an average OH functionality of 2 to 6;
wherein the ether groups are derived from, 60% to 90% of ethylene oxide units, based on the amounts of alkylene oxide units that are present in total.

* * * * *